(12) United States Patent
Robertson et al.

(10) Patent No.: US 11,628,029 B2
(45) Date of Patent: Apr. 18, 2023

(54) SURGICAL DRAPE COOLING

(71) Applicant: Intuitive Surgical Operations, Inc., Sunnyvale, CA (US)

(72) Inventors: Alec Paul Robertson, Palo Alto, CA (US); Simon Peter DiMaio, San Carlos, CA (US); Kollin Myles Tierling, Los Altos Hills, CA (US); Theodore W. Rogers, Alameda, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1254 days.

(21) Appl. No.: 16/126,102

(22) Filed: Sep. 10, 2018

(65) Prior Publication Data

US 2019/0076204 A1    Mar. 14, 2019

Related U.S. Application Data

(60) Provisional application No. 62/558,032, filed on Sep. 13, 2017.

(51) Int. Cl.
  *A61B 46/10* (2016.01)
  *A61B 34/35* (2016.01)
  (Continued)

(52) U.S. Cl.
  CPC .............. *A61B 46/10* (2016.02); *A61B 17/29* (2013.01); *A61B 34/35* (2016.02);
  (Continued)

(58) Field of Classification Search
  CPC ......... A61B 46/10; A61B 34/35; A61B 17/29; A61B 2034/305; A61B 2050/0014;
  (Continued)

(56) References Cited

U.S. PATENT DOCUMENTS 10,639,110 B2   5/2020  Hares
10,881,471 B2   1/2021  Roach et al.
(Continued)

FOREIGN PATENT DOCUMENTS

EP   3302336 A1 *  4/2018  ......... A61B 1/00142
GB   2550396 A  * 11/2017  ............. A61B 34/30

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Aaron F Roane
(74) *Attorney, Agent, or Firm* — Fish & Richardson P.C.

(57) ABSTRACT

A surgical system drape includes: a sheath having an interior cavity sized to cover a portion of a surgical system manipulator; an adaptor coupled to the sheath and including a manipulator interface and an instrument interface, the manipulator interface configured to couple with a drive interface of the manipulator, the instrument interface being configured to couple with a drive interface of a surgical instrument mounted to the manipulator; and a fluid conduit coupled to the sheath and extending within the interior cavity of the sheath, the fluid conduit configured to receive a flow of cooling fluid at a fluid port and convey the fluid along the interior cavity of the sheath to cool a component of a portion of the manipulator.

26 Claims, 10 Drawing Sheets

(51) Int. Cl.
  *A61B 17/29* (2006.01)
  *A61B 34/30* (2016.01)
  *F25D 17/08* (2006.01)
  *A61B 17/00* (2006.01)
  *A61B 50/00* (2016.01)
(52) U.S. Cl.
  CPC ............ *A61B 2017/00477* (2013.01); *A61B 2034/305* (2016.02); *A61B 2050/0014* (2016.02); *A61B 2217/007* (2013.01); *F25D 17/08* (2013.01); *F25D 2325/00* (2013.01)
(58) Field of Classification Search
  CPC .... A61B 2017/00477; A61B 2217/007; A61B 46/00; A61B 46/17; A61B 46/20; A61B 46/23; A61B 46/27; A61B 46/40; A61B 2046/236; A61B 2046/234; A61B 34/30; F25D 17/08; F25D 2325/00
  USPC ........................................................ 600/121
  See application file for complete search history.

(56) References Cited

U.S. PATENT DOCUMENTS

| | | |
|---|---|---|
| 11,051,898 B2 | 7/2021 | Zemlok et al. |
| 11,147,639 B2 | 10/2021 | Hares |
| 2020/0093556 A1 | 3/2020 | Zemlok et al. |

\* cited by examiner

SURGICAL DRAPE COOLING

TECHNICAL FIELD

This specification generally relates to surgical drapes for use with teleoperated robotic surgical systems. In particular, various embodiments are directed to surgical drapes that facilitate circulation of cooling fluid proximate a portion of a surgical system manipulator.

BACKGROUND

Minimally invasive medical techniques (e.g., laparoscopy) have been used to reduce the amount of extraneous tissue which may be damaged during diagnostic or surgical procedures, thereby reducing patient recovery time, discomfort, and deleterious side effects. Such techniques were traditionally performed manually via a surgeon manipulating various surgical instruments within the patient's body but can now by implemented using teleoperated robotic systems that provide telepresence. Performing minimally invasive surgery with teleoperated robotic systems facilitates increased precision and range of motion in manipulating surgical instruments when compared to manual techniques, but also introduces new challenges. One such challenge is the need to erect a sterility barrier between certain non-sterile portions of the surgical system (e.g., portions housing the various motors, sensors, encoders, and electrical connections that cannot withstand a sterilization process) and the area immediately adjacent the patient. One solution to this particular challenge has been to cover the non-sterile portions of the system with a sterile drape, leaving a sterilized instrument to be manipulated by the system uncovered, so that it can be easily replaced by another instrument during a surgical procedure.

SUMMARY

In one aspect, a surgical system drape includes: a sheath having an interior cavity sized to cover a portion of a surgical system manipulator; an adaptor coupled to the sheath and including a manipulator interface and an instrument interface, the manipulator interface configured to couple with a drive interface of the manipulator, the instrument interface being configured to couple with a drive interface of a surgical instrument mounted to the manipulator; and a fluid conduit coupled to the sheath and extending within the interior cavity of the sheath, the fluid conduit configured to receive a flow of cooling fluid at a fluid port and convey the fluid along the interior cavity of the sheath to cool a component of a portion of the manipulator.

In some examples, the sheath includes an impervious structure having interior and exterior surfaces, the interior surface associated with the fluid conduit, and the exterior surface being in a sterile state.

In some examples, the fluid conduit includes a tube attached to an interior surface of the sheath.

In some examples, the fluid conduit includes a passageway having opposing continuous edges defined between two seams attaching adjacent layers of the sheath. In some examples, the sheath includes an outermost layer, an innermost layer, and a middle layer between the outermost and innermost layers, and the passageway is formed between the middle layer and the innermost layer. In some examples, the surgical system drape further includes a hollow sump pocket formed between the outermost layer and the middle layer.

In some examples, the fluid conduit includes a vent located adjacent the portion of the manipulator and positioned to expel cooling fluid conveyed by the fluid conduit into contact with the manipulator. In some examples, the vent includes a plurality of apertures distributed along a length of the fluid conduit. In some examples, the plurality of vent apertures is configured to expel more cooling fluid at a first location along the length of the fluid conduit than at a second location, the first location located at a closer proximity to the adaptor than the second location.

In some examples, at least a portion of the sheath includes a tubular-shaped structure, and the fluid conduit is arranged in a helical shape traversing the tubular shape along a length of the sheath.

In some examples, the fluid conduit is configured to provide sufficient structural support to separate the sheath from a surface of the manipulator covered by the sheath. In some examples, the fluid conduit is configured to inflate in response to internal pressure of flowing cooling fluid and apply a hoop-stress from the internal pressure to provide the structural support. In some examples, the fluid conduit includes an outer wall having sufficient strength to provide the structural support. In some examples, the fluid conduit is arranged to provide less structural support of the sheath adjacent an articulating joint of the manipulator than adjacent a link of the manipulator.

In some examples, the cooling fluid conduit is shaped to engage a surface feature of the manipulator to align the drape with the manipulator.

In some examples, the surgical system drape further includes a guide member coupled with the sheath, the guide member configured to engage a portion of the manipulator to self-align one or more vents along the fluid conduit with one or more cooling channels on the manipulator.

In another aspect, a computer assisted surgical system includes: a robotically operable surgical manipulator including a manipulator drive interface; a surgical instrument coupled to the manipulator and including an instrument drive interface; and a surgical drape forming a sterility barrier between a sterile surgical field and a portion of the manipulator. The drape includes: a sheath having an interior cavity sized to cover the portion of the manipulator to form the sterility barrier; an adaptor coupled to the sheath and including a manipulator interface and an instrument interface, the manipulator interface configured to engage the manipulator drive interface, and the instrument interface configured to engage the instrument drive interface; and a fluid conduit integrated with the sheath and extending within the interior cavity of the sheath, the fluid conduit configured to receive a flow of cooling fluid at a fluid port and convey the fluid along the interior cavity of the sheath to cool a component of the manipulator.

In some examples, the fluid conduit includes a vent located adjacent the portion of the manipulator and positioned to expel cooling fluid conveyed by the fluid conduit into contact with the manipulator. In some examples, the manipulator includes a surface feature configured to route cooling fluid expelled by the vent to the component of the portion of the manipulator, the component residing at a remote location within the interior cavity relative to the vent. In some examples, the manipulator further includes a magnetic alignment member, and the drape further includes a magnetically attractable guide member, such that the alignment member attracts the guide member to facilitate guided alignment of the vent aperture of the fluid conduit and the surface feature of the manipulator.

In some examples, the fluid conduit is configured to provide sufficient structural support to separate the sheath from a surface of the manipulator covered by the sheath. In some examples, the fluid conduit is configured to inflate in response to internal pressure of flowing cooling fluid and apply a hoop-stress from the internal pressure to provide the structural support.

In some examples, the surgical system further includes a pressurized cooling fluid source fluidly coupled to the fluid port and configured to urge the flow of cooling fluid to move along the fluid conduit with sufficient pressure to inflate the fluid conduit.

In some examples, the surgical system further includes a vacuum pressure source fluidly coupled to the fluid conduit and configured to urge the flow of cooling fluid to move downstream along the fluid conduit away from the fluid port.

In some examples, the manipulator includes a surface feature engaging the cooling fluid conduit to align the surgical drape with the manipulator. In some examples, the surface feature includes a channel receiving the fluid conduit.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

One or more of the illustrated elements may be exaggerated to better show the features, process steps, and results. Like reference numbers and designations in the various drawings may indicate like elements.

DETAILED DESCRIPTION

Embodiments of the present disclosure relate to surgical drapes for use with teleoperated robotic surgical systems. In particular, the surgical drapes described throughout this disclosure are appropriately configured (e.g., shaped and sized) to cover one or more unsterilized portions of a surgical instrument manipulator in order to inhibit or prevent contamination of a surrounding sterile surgical site. More specifically, the presently-described embodiments are derived from a realization that certain conventional surgical drapes have a tendency to snag to the teleoperated instrument manipulator. When a surgical drape snags to an articulating instrument manipulator, (1) the drape is more susceptible to failure (e.g., tearing, ripping, puncture) as the manipulator moves, and (2) airflow through the interior of the drape is restricted. Air flow restrictions significantly degrade heat dissipation and lead to the formation of "hot spots" along the manipulator's exterior surfaces during use. The development of hot spots during a surgical procedure can be particularly problematic when the instrument manipulator includes one or more motor-driven joints, such as described in U.S. Pat. No. 8,004,229, for example. Accordingly, the present disclosure describes complementary surgical drapes and surgical instrument manipulators equipped with features that inhibit snagging of the drape and/or actively promote heat dissipation along the manipulator.

Minimally invasive surgery can be performed by inserting surgical instruments through orifices in a patient's body (e.g., natural orifices or body-wall incisions) and controlling the surgical instruments via an interface on the outside of the body. In various embodiments of the present disclosure, the surgical instruments are teleoperated by surgeons. Thus, the surgeons do not move the instruments by direct physical contact, but instead control instrument motion from some distance away by moving master controllers ("masters"). The operating surgeon is typically provided with a view of the actual surgical site via a visual display, so that the surgeon may remotely perform surgical motions on the masters while viewing the surgical site. A controller of the surgical system causes the surgical instrument to be moved in accordance with movement of the masters.

Figure 1:
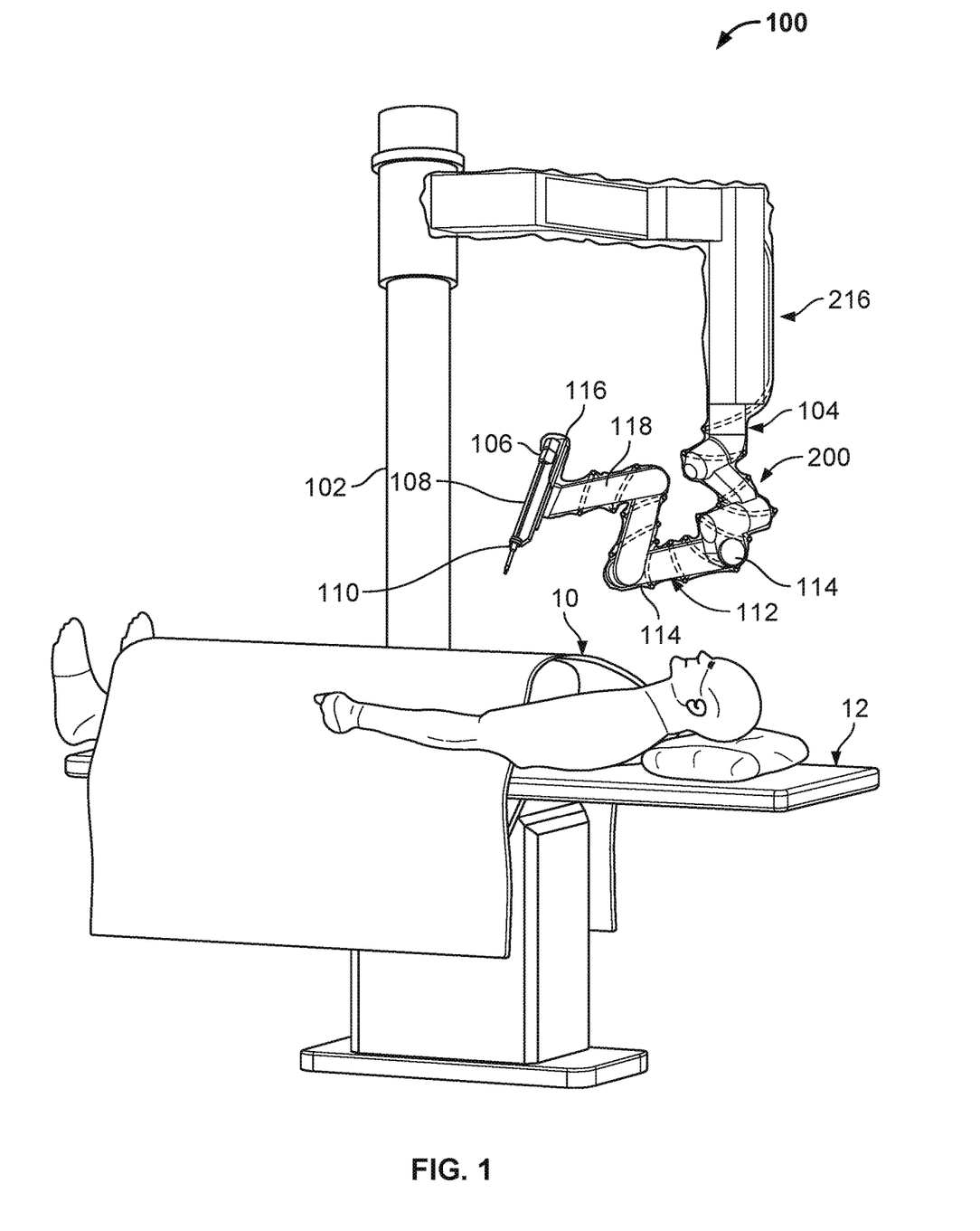
FIG. 1 is a perspective view of a portion of a teleoperated surgical system.

FIG. 1 depicts a patient-side portion 100 of a teleoperated surgical system in accordance with one or more embodiments of the present disclosure. Patient-side portion 100 is a robotic system for performing minimally invasive surgery on a patient's body 10 positioned on an operating table 12. Patient-side portion 100 includes a column 102, a support assembly 104, an instrument manipulator 112, and an instrument carriage 106. In this example, column 102 anchors patient-side portion 100 on a floor surface (not shown) proximate operating table 12. However, in other embodiments, the patient-side portion may be mounted to a wall, to the ceiling, to the operating table supporting the patient's body, or to other operating room equipment.

Support assembly 104 branches radially outward from column 102 to couple with instrument manipulator 112. Instrument carriage 106 resides at a distal end of instrument manipulator 112. Instrument carriage 106 supports a detachable surgical instrument 108. Accordingly, instrument carriage 106 includes various actuators and control connections for actively controlling functionality of surgical instrument 108 within patient body 10 during a surgical procedure. In particular, the teleoperated actuators housed in instrument carriage 106 provide a number of controller motions that surgical instrument 108 translates into a corresponding variety of movements of the instrument's end effector.

An entry guide 110 (e.g., a cannula) serves as a surgical port to an orifice of patient body 10 that receives surgical instrument 108 to guide the instrument into the patient. Entry guide 110 may perform various other functions, such as allowing fluids and other materials to pass into or out of the body, and reducing trauma at the surgical site by isolating at least some motion (e.g., translating movement along an insertion axis and axial rotation of the instrument shaft) of surgical instrument 108 from the body wall.

The term "surgical instrument" is used herein to describe a medical device for insertion into a patient's body and use in performing surgical or diagnostic procedures. A surgical instrument typically includes an end effector associated with one or more surgical tasks, such as forceps, a needle driver, a shears, a bipolar cauterizer, a tissue stabilizer or retractor, a clip applier, an anastomosis device, an imaging device (e.g., an endoscope or ultrasound probe), and the like. Some surgical instruments used with embodiments of the present disclosure further provide an articulated support (sometimes referred to as a "wrist") for the end effector so that the position and orientation of the end effector can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored information (e.g., on a semiconductor memory inside the instrument) that may be permanent or may be updatable by the surgical system. Accordingly, the system may provide for either one-way or two-way information communication between the instrument and one or more system components. Surgical instruments appropriate for use in one or more embodiments of the present disclosure may control their end effectors (surgical tools) with one or more rods and/or flexible cables. In some examples, rods, which may be in the form of tubes, may be combined with cables to provide a "push/pull" control of the end effector, with the cables providing flexible sections as required. A typical elongate shaft for a surgical instrument is small, perhaps five to eight millimeters in diameter. The diminutive scale of the mechanisms in the surgical instrument creates unique mechanical conditions and issues with the construction of these mechanisms that are unlike those found in similar mechanisms constructed at a larger scale, because forces and strengths of materials do not scale at the same rate as the size of the mechanisms. The rods and cables must fit within the elongate shaft and be able to control the end effector through the wrist joint.

Figure 2:
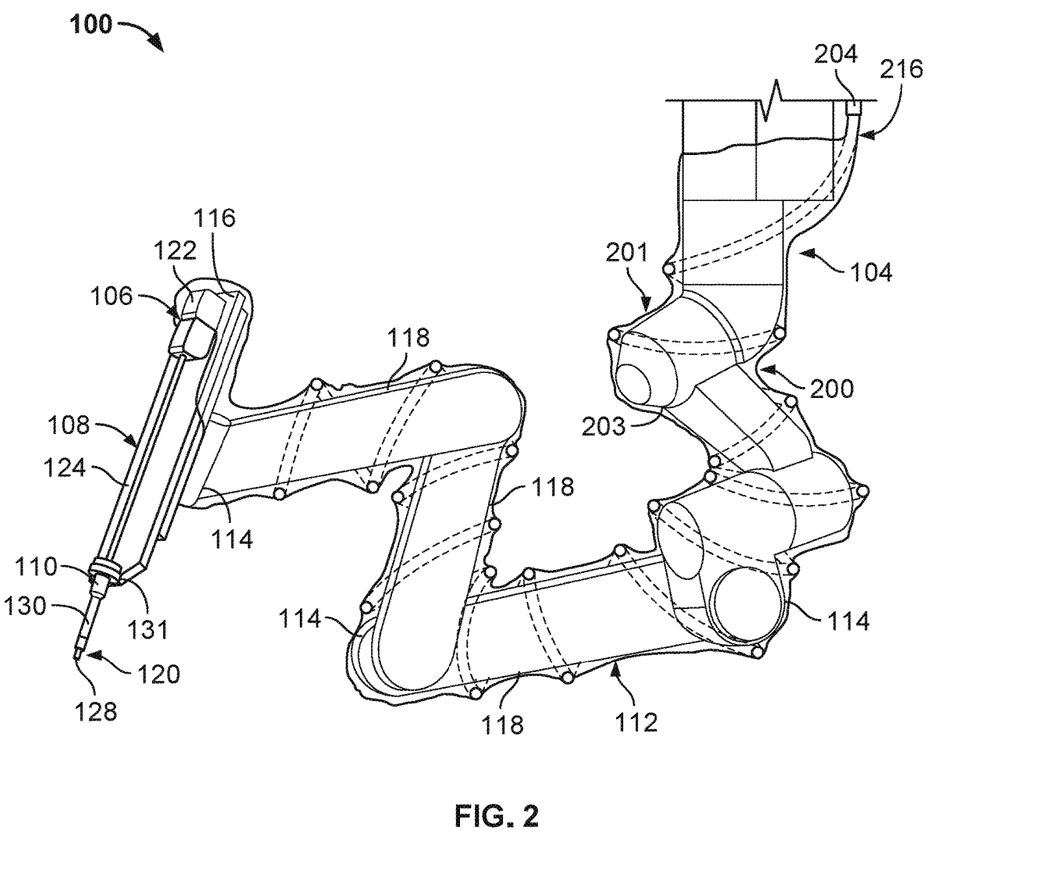
FIG. 2 is a perspective view of an instrument manipulator carrying a surgical drape.

Referring to FIGS. 1 and 2, instrument manipulator 112 may be provided in a variety of forms that allow surgical instrument 108 to move with one or more mechanical degrees of freedom (e.g., all six Cartesian degrees of freedom, five or fewer Cartesian degrees of freedom, etc.). Typically, instrument manipulator 112 is controlled to move surgical instrument 108 around a particular remote center of motion that remains stationary with reference to patient's body 10. This center of motion is typically located proximate where surgical instrument 108 enters patient body 10 (e.g., at some point along entry guide 110, such as the midpoint of the body wall).

In this example, instrument manipulator 112 includes a plurality of manipulator links 118, joints 114 situated between adjacent manipulator links 118, and an elongated spar 116. Spar 116 carries and supports instrument carriage 106 and entry guide 110. Instrument carriage 106 is mounted to ride along the length of spar 116, while entry guide 110 is held fixed by a connector 131 at the distal end of spar 116. Note, in the context of this disclosure, proximal means farther away from the surgical site (i.e., near support assembly 104), and distal means closer to the surgical site (i.e., near instrument carriage 106). Movement of instrument carriage 106 effects identical translating movement of surgical instrument 108 through the stationary entry guide 110 along an insertion axis relative to patient body 10.

Joints 114 facilitate the articulated movement of manipulator links 118 to locate surgical instrument 108 at a desired angular orientation with multiple degrees of freedom (e.g., yaw, pitch, and roll) about the remote center of motion. Furthermore, as described above, the translating movement of instrument carriage 106 along spar 116 locates surgical instrument 108 at a desired insertion point through that center of motion. Thus, the various teleoperated actuators of instrument manipulator 112 move surgical instrument 108 as a whole, while the teleoperated actuators housed within instrument carriage 106 move only the instrument's end effector or other individual instrument components. In some examples, movement of joints 114 is constrained to maintain the center of motion of manipulator 112 by fixed intersecting axes (hardware-centering). In some other examples, movement of joints 114 is constrained by software-controlled motors (software-centering). As noted above, implementations employing the software-centering motor-driven joints may especially benefit from embodiments described below that enhance heat dissipation along instrument manipulator 112.

Figures 2A, 2B:
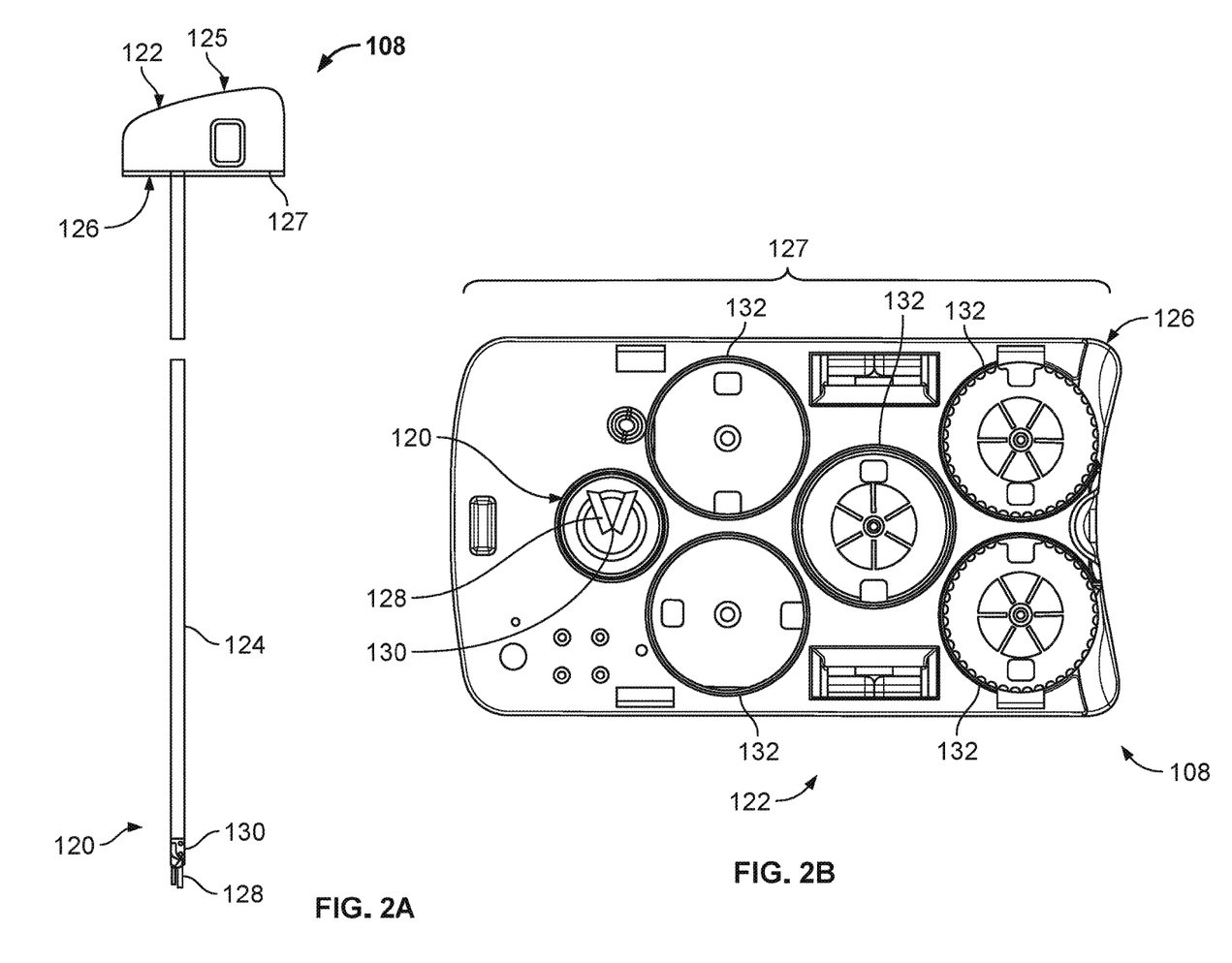
FIG. 2A is a side view of a surgical instrument including a drive assembly.
FIG. 2B is a bottom view of the drive assembly of FIG. 2A.

Referring now to FIGS. 2A and 2B, surgical instrument 108 includes a distal portion 120 and a drive assembly 122 coupled to one another by an elongate shaft 124 defining an internal bore. Drive assembly 122 includes a housing 125 supporting an input device 126. Input device 126 includes an instrument drive interface 127. The input device facilitates controlled adjustment of the instrument's end effector via one or more drive cables extending along the internal bore of the elongate instrument shaft.

Drive interface 127 provides mechanical connections to the other control features of surgical instrument 108. During use, instrument drive interface 127 couples to a complementary drive interface of instrument carriage 106 (e.g., manipulator drive interface 4 shown in FIG. 3) through an adaptor (e.g., adaptor 220), which allows instrument carriage 106 to control surgical instrument 108 in the manner generally described above. Distal portion 120 of surgical instrument 108 may provide any of a variety of surgical tools, such as the forceps 128 shown, a needle driver, a cautery device, a cutting tool, an imaging device (e.g., an endoscope or ultrasound probe), or a multipart device that includes a combination of two or more various tools and imaging devices. Further, in the illustrated embodiment, forceps 128 are coupled to elongate shaft 124 by a wrist joint 130, which allows the orientation of the forceps to be manipulated with reference to the elongate shaft 124.

The bottom view of surgical instrument 108 shown in FIG. 2B illustrates instrument drive interface 127. As shown, drive interface 127 includes a set of five steering inputs 132, each of which governs a different aspect of movement by wrist joint 130 and forceps 128. Of course, more or less steering inputs 132 can be provided in different implementations. When drive interface 127 is coupled to instrument carriage 106, each of steering inputs 132 interfaces with an actuator that drives the steering input. In this example, steering inputs 132 are configured to form a direct-drive (i.e., absent speed reduction) mechanical engagement with respective rotary actuators (e.g., servo motors) of instrument carriage 106 through the adaptor. However, other suitable configurations for power transmission can also be used (e.g., mechanical couplings including speed and/or torque converters, fluid couplings, and/or electrical couplings). Each of steering inputs 132 is part of a drive shaft (not shown) that operates a drive cable (not shown) controlling movement of forceps 128.

Referring back to FIGS. 1 and 2, patient-side portion 100 further includes a surgical drape 200 covering manipulator 112, including joints 114 and spar 116. Surgical drape 200 forms a sterility barrier between a sterile surgical field and the unsterilized instrument manipulator 112. In this example, in addition to manipulator 112, drape 200 covers a portion of support assembly 104, extending the sterility barrier to partially shield this component from the sterile field as well. The present disclosure, however, is not limited to any particular configuration in this regard. That is, in certain other examples, drape 200 may cover only the manipulator 112, only a portion of manipulator 112, or may extend to cover a larger portion of support assembly 104. In any event, components of patient-side portion 100 that are not covered by drape 200 (e.g., surgical instrument 108, entry guide 110, and part of instrument carriage 106) will generally be sterile. In some examples, one or more of these sterile components are capable of being sterilized and re-used. In some examples, one or more of these components are disposable, provided in hermetically sealed packages (e.g., peel-open pouches or sterilization wraps).

As shown in FIG. 2, surgical drape 200 includes a sheath 201 and a fluid conduit 216. Sheath 201 is a flexible, bag-like object having an opening that leads to an interior cavity 203. Interior cavity 203 is appropriately shaped and sized to receive manipulator 112. Sheath 201 is an impervious structure having an interior (i.e., innermost) surface and an exterior (i.e., outermost) surface. During use, the exterior surface of sheath 201 is exposed to the sterile surgical field, and, therefore, is provided in a sterile state. Sheath 201 and/or fluid conduit 216 may be formed from a suitable plastic material (e.g., thermoplastic polyurethane) or any other flexible material capable of withstanding a sterilization process. As such, in some implementations, surgical drape 200 may be re-used over multiple surgical procedures following sterilizations. In other implementations, however, surgical drape 400 is adapted to be sterilized for a single use (e.g., by gamma irradiation).

Fluid conduit 216 is associated with the interior surface of sheath 201, such that fluid conduit 216 extends within interior cavity 203 of sheath 201. This means that fluid conduit 216 resides proximate manipulator 112 when manipulator 112 is covered by surgical drape 200. In this example, fluid conduit 216 is configured to receive a flow of cooling fluid at a fluid port 204. Fluid port 204 is fluidically coupled to a cooling fluid source (not shown), which may include a reservoir of cooling fluid and a positive pressure source (e.g., a pump) for circulating fluid downstream to and through fluid conduit 216. The fluid source may reside locally near the surgical site or at a remote location. In certain other examples, the fluid conduit may be fluidically coupled to a vacuum pressure source that draws cooling fluid upstream through the fluid conduit. In any event, fluid conduit 216 conveys cooling fluid along the interior cavity of sheath 201 to transfer heat generated by one or more components of manipulator 112 (e.g., motor-driven joints 114). In some examples, the cooling fluid is a gas-phase coolant, such as air, hydrogen, or inert gas. In some other examples, the cooling fluid is a liquid-phase coolant, such as water, oil, freon, or refrigerant. In still some further examples, the cooling fluid may undergo a phase change during use.

In some examples, fluid conduit 216 provides sufficient structural support to separate sheath 201 from the surface of manipulator 112. For instance, fluid conduit 216 may become inflated in response to internal pressure from the flowing cooling fluid. More specifically, hoop-stress imparted on the outer walls of fluid conduit 216 from the internal pressure of the cooling fluid may initiate inflation, which provides adequate structural support to raise the interior surface of sheath 201 above the outer surface of manipulator 112. As another example, the outer wall of fluid conduit 216 may have sufficient strength to provide the requisite structural support (e.g., via its material stiffness properties or thickness) absent inflation by the cooling fluid. In some implementations, it may be advantageous to maintain sheath 201 in a spaced-apart relationship with manipulator 112 in order to inhibit drape 200 from snagging to manipulator 112 as it moves and articulates during a surgical procedure. In some implementations, the fluid conduit can be appropriately designed to provide less structural support adjacent the articulating joints of the manipulator than adjacent a link of the manipulator so as not to inhibit operation of the joints.

Figure 3:
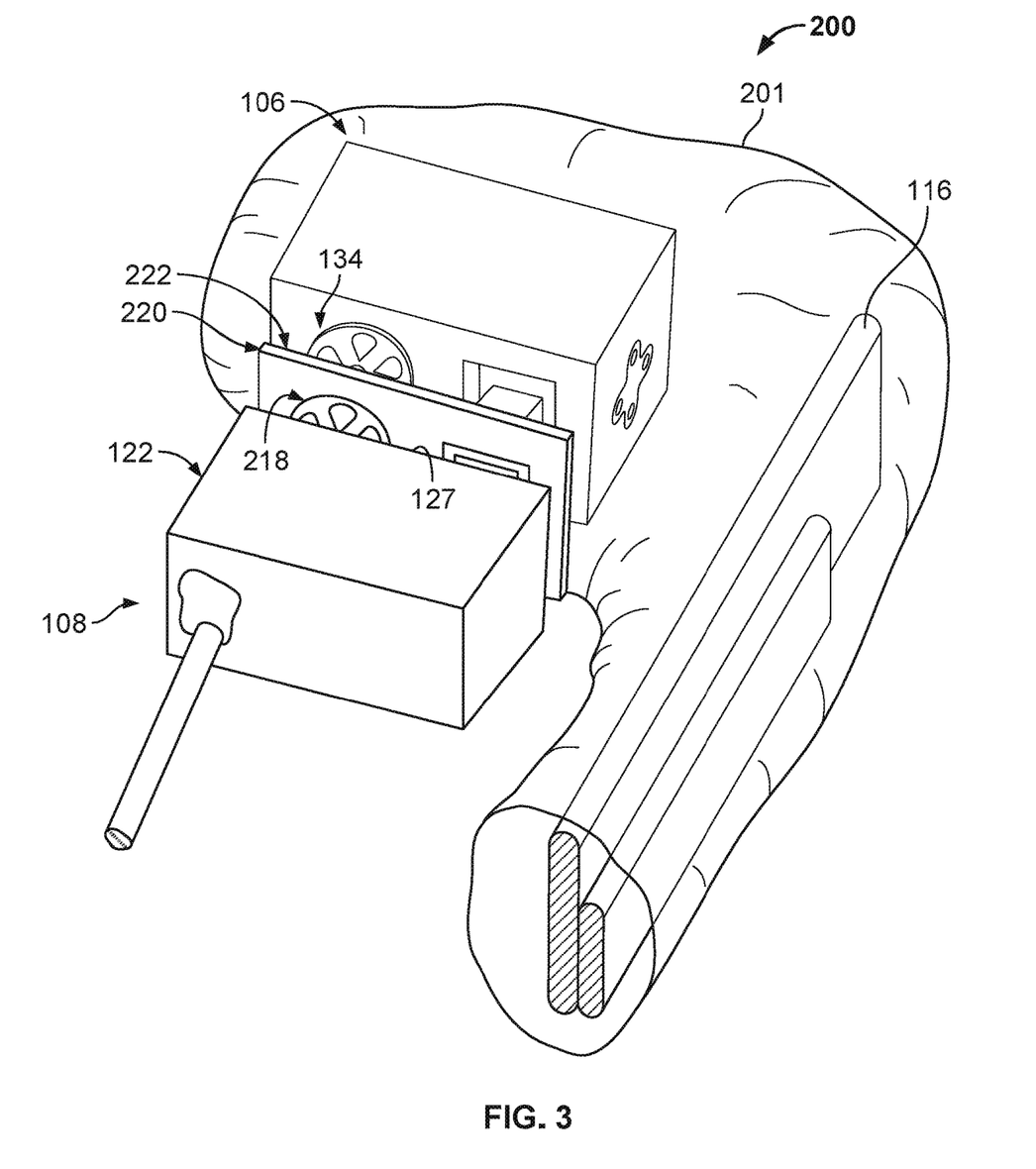
FIG. 3 is a perspective exploded view of a surgical drape, an instrument carriage, and a spar.

As shown in FIG. 3, surgical drape 200 further includes an adaptor 220 coupled to an end portion of sheath 201. In this example, adaptor 220 is permanently bonded to sheath 201, but other physical attachment mechanisms are also contemplated. For example, the adaptor may be fixed to the sheath by mechanical fasteners, adhesives, etc. Adaptor 220 provides physical connection point for drape 200, spar 116, and surgical instrument 108. This connection point secures sheath 201 in place covering manipulator 112 during a surgical procedure. In this example, adaptor 220 is provided in the form of a relatively thin plate-like body having two opposite substantially planar faces. A first face of adaptor 220 includes an instrument interface 218, and a second face includes a manipulator interface 222. When the various components are assembled, adaptor 220 is sandwiched between instrument carriage 106 and drive assembly 122 of surgical instrument 108. In the assembled condition, the adaptor's manipulator interface 222 engages a drive interface 134 of instrument carriage 106, and the adaptor's instrument interface 218 engages drive interface 127 of instrument drive assembly 122. The respective interfaces 218,222 of adaptor 220 are configured to transfer torque and power from the actuators of instrument carriage 106 to steering inputs 132 of drive interface 127.

Figures 4A, 4B:
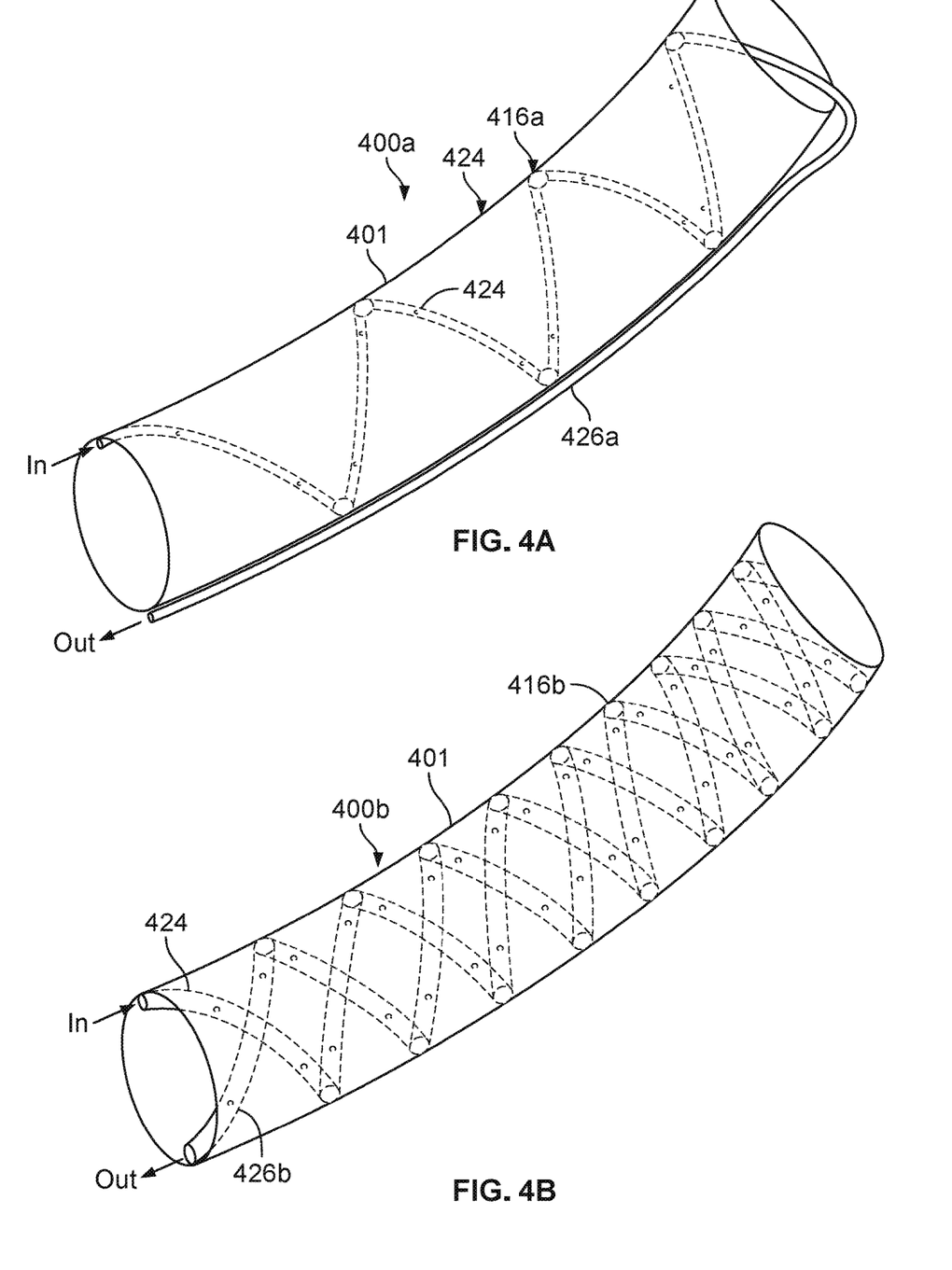
FIG. 4A is a perspective side view of a first example surgical drape having a helical fluid conduit.
FIG. 4B is a perspective side view of a second example surgical drape having a double-helical fluid conduit.

FIGS. 4A and 4B illustrate two example surgical drapes 400a, 400b in accordance with various embodiments of the present disclosure. As shown, each of surgical drapes 400a,b includes a tubular sheath 401 and a fluid conduit 416a, 416b integrated with sheath 401. In these examples, fluid conduit 416a,b is provided in the form of a separate tube physically attached to sheath 401. However, in some other examples a suitable fluid conduit may include a passageway formed between two or more layers of the sheath (see, e.g., FIGS. 5D, 5E, 6D). Fluid conduit 416a,b includes a supply conduit portion 424 extending along the interior surface of sheath 401 and a return conduit portion 426a,b extending along the exterior surface of sheath 401. Supply conduit portion 424 receives a flow of cooling fluid from an inlet fluid port (not shown) and conveys the cooling fluid in a downstream direction (i.e., away from the fluid port/source) through the interior cavity of sheath 401. In each of the illustrated examples, supply conduit portion 424 is arranged in a helical configuration. In some implementations, the helical arrangement is advantageous because it distributes the flow of cooling fluid evenly throughout the interior cavity of sheath 401. Return conduit portion 426a,b conveys the cooling fluid in an upstream direction towards a fluid return port (not shown). In the example of FIG. 4A, return conduit portion 426a is shown extending along the exterior surface of sheath 401, though it can also extend along the interior surface. Having a return conduit may be particularly advantageous in implementations where the ability of the cooling fluid to dissipate heat is exhausted relatively quickly and continued exposure to the instrument manipulator provides little to no added value from a heat-exchange perspective. In the example of FIG. 4B, return conduit portion 426b is arranged in a helical configuration extending along the interior surface of sheath 401. This configuration may be advantageous in implementations where the cooling fluid has a relatively high capacity for dissipating heat, and extended dwell time proximate the manipulator results in increased cooling.

Figure 5A:
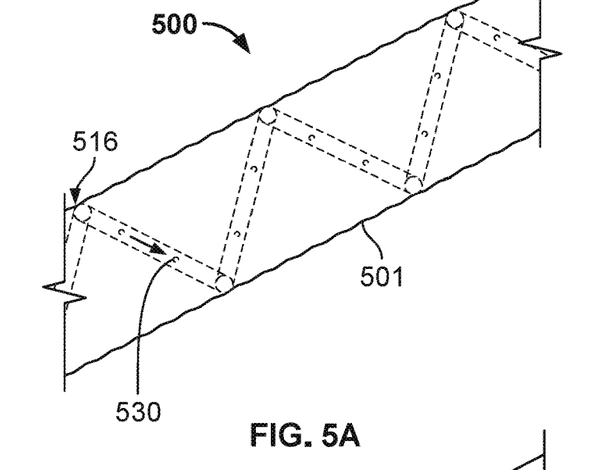
FIG. 5A is a side view of a portion of a third example surgical drape having a fluid conduit arranged in a helical configuration.
Figure 5B:
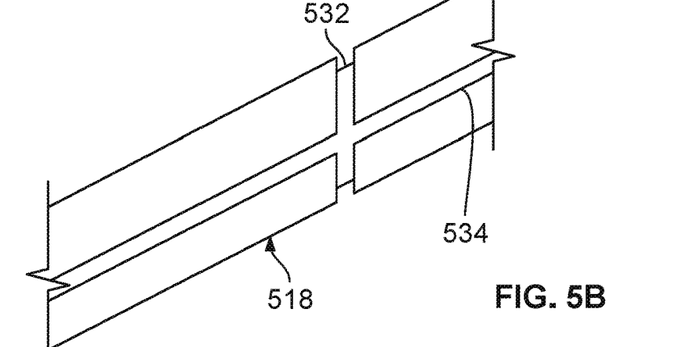
FIG. 5B is a side view of a portion of a first example surgical instrument manipulator having circumferential and an axial cooling channels.
Figure 5C:
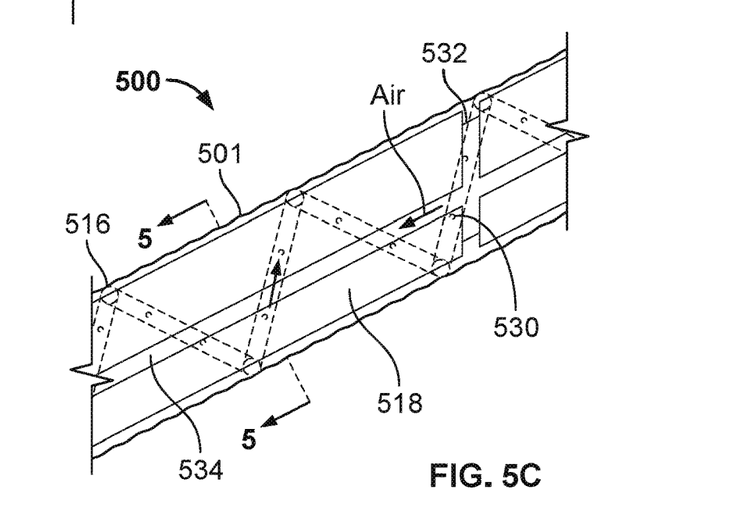
FIG. 5C is a side view of the first example manipulator of FIG. 5B carrying the third example surgical drape of FIG. 5A.

FIGS. 5A-5C illustrate a complementary surgical drape 500 and manipulator link 518 in accordance with one or more embodiments. FIGS. 5A and 5B illustrate drape 500 and manipulator link 518 in isolation; and FIG. 5C illustrates drape 500 covering manipulator link 518. Note, drape 500 is similarly configured to drape 400a described above with reference to FIG. 4A. Accordingly, drape 500 includes a tubular sheath 501 and a fluid conduit 516 arranged in a helical configuration along the interior surface of sheath 501. In this example, fluid conduit 516 includes a plurality of vents 530 distributed along its length. Vents 530 are provided in the form of rounded apertures (e.g., circular or oval-shaped openings) extending through the outer wall defining fluid conduit 516. As the cooling fluid is conveyed through fluid conduit 516, vents 530 expel a portion of the cooling fluid into direct contact with manipulator link 518. In some implementations, direct contact between the cooling fluid and the manipulator link can enhance the rate and degree of heat dissipation. In this example, vents 530 are of approximately the same shape and size, and are distributed at regular intervals along fluid conduit 516. However, in certain other examples, the shape, size, and distribution density of the vents may vary. For example, the vents may have a larger open area or may have a greater distribution density proximate locations of the manipulator that tend to generate a greater amount of heat (e.g., along the spar near the electro-mechanical components of the instrument carriage, or near the motor-controlled joints). As another example, the shape/size and distribution density of the vents may be selected to regulate the flow rate of cooling fluid through the fluid conduit.

Manipulator link 518 includes surface features appropriately configured to route cooling fluid expelled from vents 530 to remote targeted portions of the manipulator (e.g., locations proximate components that generate heat). In this example, the surface features are provided in the form of a circumferential cooling channel 532 and an axial cooling channel 534. As shown, circumferential cooling channel 532 runs transverse to the length of manipulator link 518, and axial cooling channel 534 extends parallel to the lengthwise direction. In certain implementations, the cooling channels may vary in depth and shape in order to effectively route cooling fluid to different locations of the manipulator components. As shown in FIG. 5C, when drape 500 covers manipulator link 518, a subset of vents 530 are aligned with circumferential and axial cooling channels 532,534. At these locations, cooling fluid is expelled from fluid conduit 516 and routed along cooling channels 532,534 to remote portions of manipulator link 518.

Figure 5D:
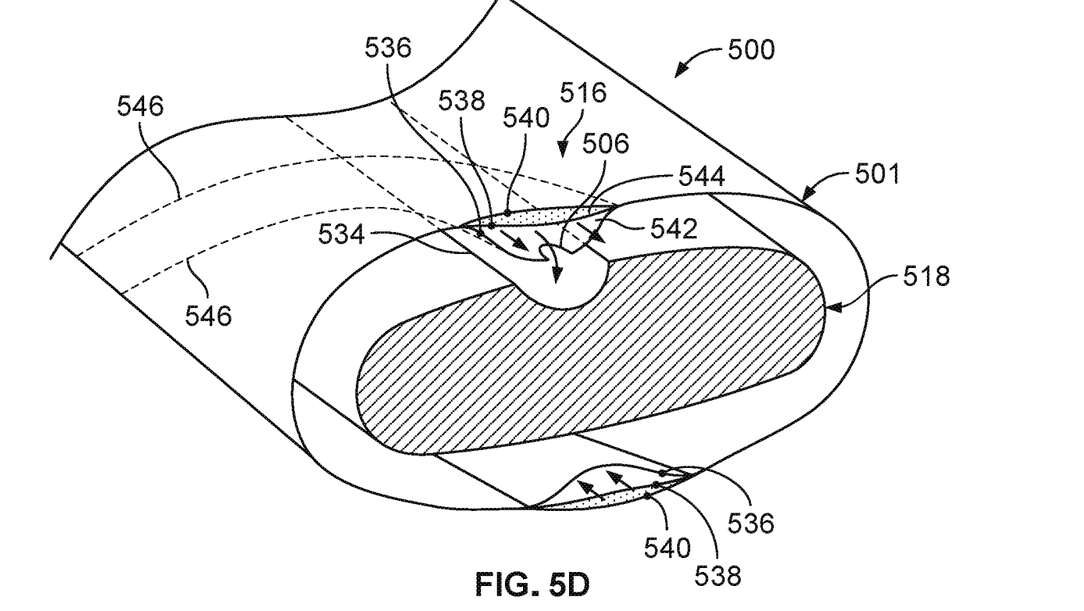
FIG. 5D is a cross-sectional perspective view of the first example manipulator and the third example surgical drape of FIG. 5C taken along the plane marked 5-5 in FIG. 5C.
Figure 5E:
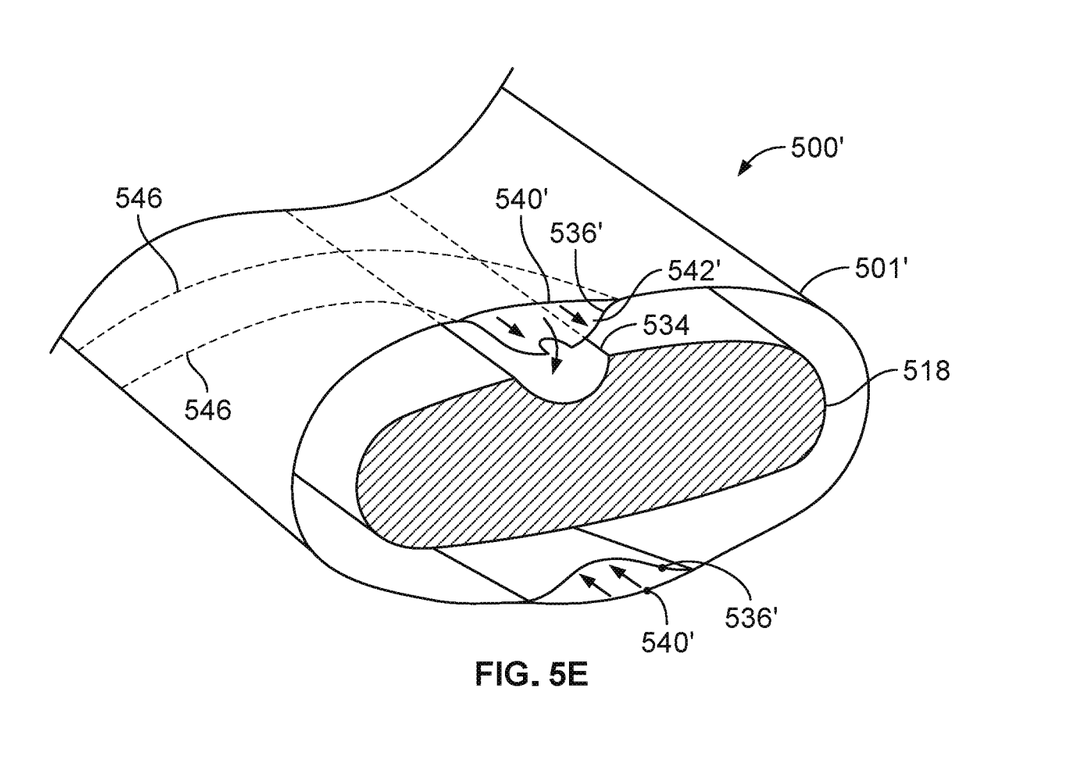
FIG. 5E is a cross-sectional perspective view of the first example manipulator of FIGS. 5B and 5C carrying a fourth example surgical drape.

Referring now to FIG. 5D, in this example, sheath 501 includes three distinct layers: an outermost layer 540, a middle layer 538, and an innermost layer 536. Fluid conduit 516 includes a passageway 542 for receiving the flow of cooling fluid and a hollow sump pocket 544. As shown, passageway 542 is formed by opposing continuous edges defined between two seams 546 attaching adjacent layers of sheath 501, namely middle layer 538 and innermost layer 536. Sump pocket 544 is similarly formed by seams 546 between outermost layer 540 and middle layer 538. The co-extensive arrangement of sump pocket 544 and passageway 542 provides a measure of protection against contamination of the sterile field. For example, if middle layer 538 is compromised during use (e.g., punctured or torn), sump pocket 544 would receive at least a portion of the cooling fluid, preventing the fluid from escaping into a sterile field. FIG. 5E shows a similar example, where a drape 500' features a sheath 501' made of two layers, an innermost layer 536' and an outermost layer 540', which form the passageway 542' for receiving and conveying cooling fluid.

Figure 6A:
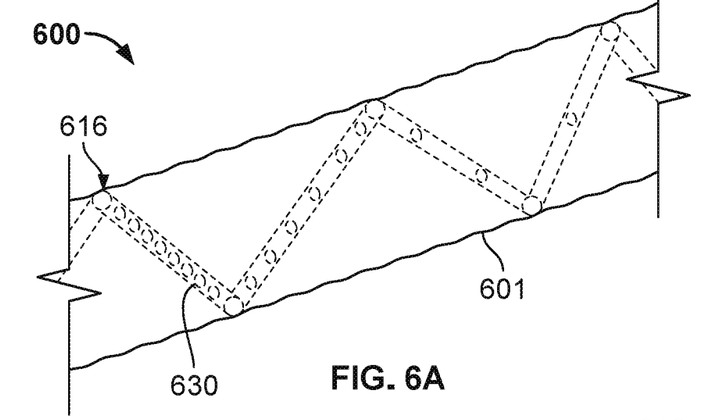
FIG. 6A is a side view of a portion of a fifth example surgical drape having a fluid conduit arranged in a helical configuration.
Figure 6B:
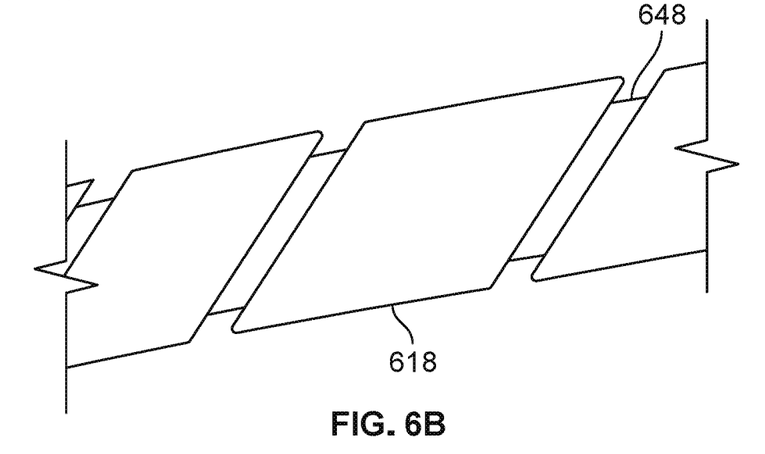
FIG. 6B is a side view of a portion of a second example surgical instrument manipulator having a helical cooling channel.
Figure 6C:
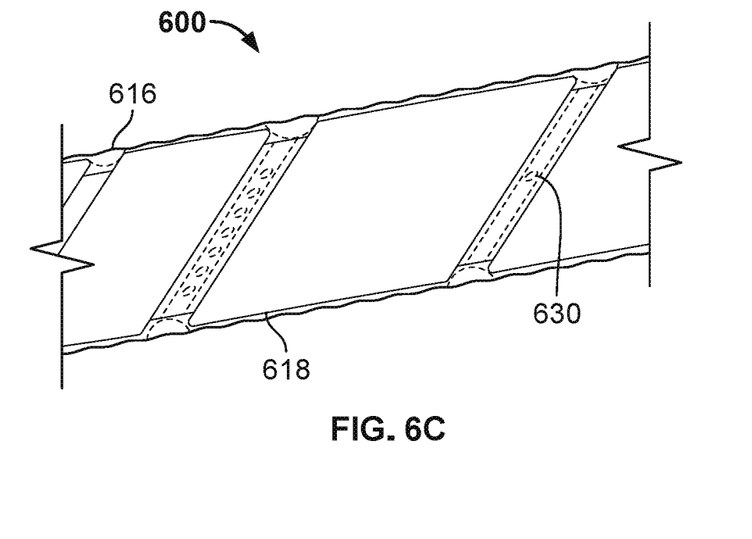
FIG. 6C is a side view of the second example manipulator of FIG. 6B carrying the fifth example surgical drape of FIG. 6A.

FIGS. 6A-6C illustrate a similar example drape 600 and manipulator link 618 as described above with reference to FIGS. 5A-5C. In this example, however, drape 600 includes a sheath 601 supporting a fluid conduit 616 having a varying distribution of vents 630. Here, vents 630 are distributed at a greater density (i.e., spaced more closely together) at the proximal end of sheath fluid conduit 616 than at its distal end. Further, in this example, manipulator link 618 features a helical cooling channel 648 that substantially matches the helical configuration of fluid conduit 616. Cooling channel 648 is configured (e.g., appropriately sized and shaped) to at least partially receive fluid conduit 616. Engaging fluid conduit 616 with cooling channel 648 aligns drape 600 with manipulator link 618, such that each of the conduit vents 630 is permitted to expel cooling fluid directly into cooling channel 648. Moreover, because fluid conduit 616 is seated within cooling channel 648, sheath 601 is placed in closer proximity to manipulator link 618 to provide a relatively tight-fitting drape 600. The tight-fitting drape may be particularly advantageous in certain implementations where a larger, loose-fitting drape may snag onto other objects or structures within the operating room and/or may obscure the field of view for human users or sensors within the operating room.

Figure 7A:
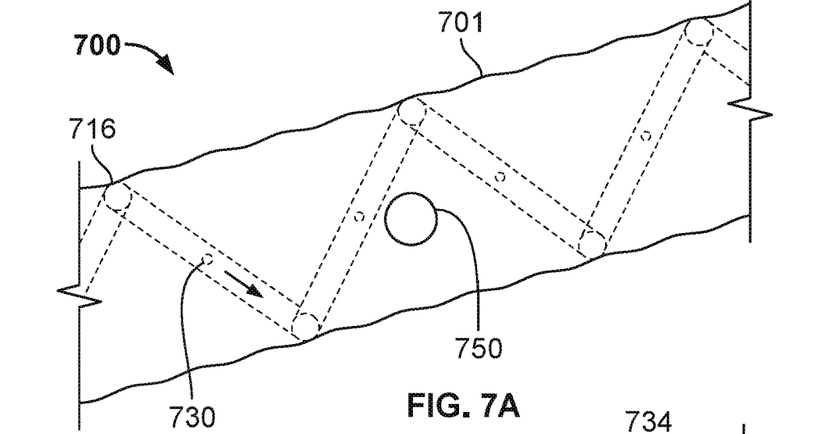
FIG. 7A is a side view of a portion of a sixth example surgical drape having a magnetic member located near an orifice of a helical fluid conduit.
Figure 7B:
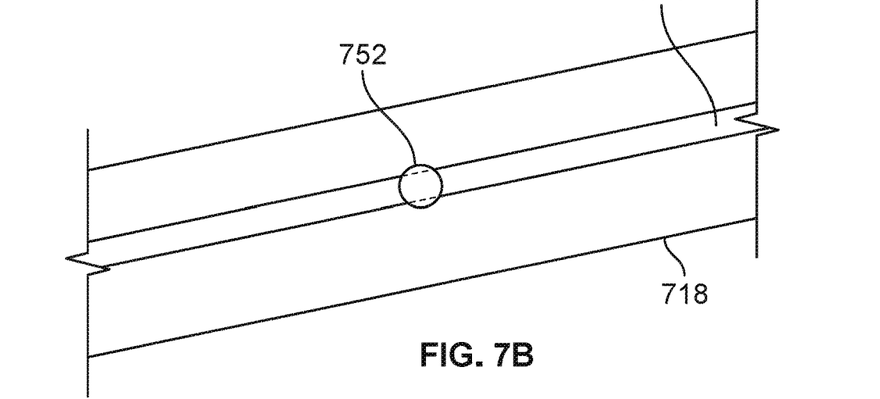
FIG. 7B is a side view of a portion of a third example surgical instrument manipulator having a magnetic member located near an axial cooling channel.
Figure 7C:
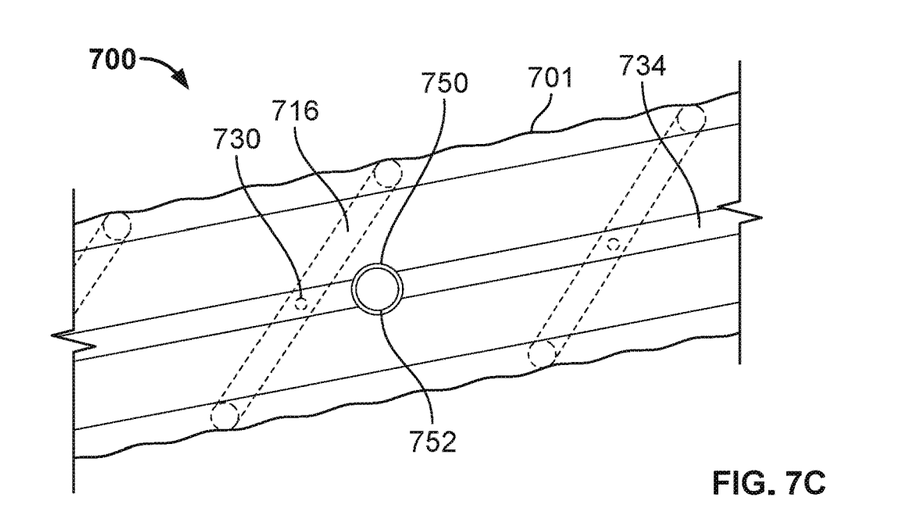
FIG. 7C is a side view of the third example manipulator of FIG. 7B carrying the sixth example drape of FIG. 7A.

FIGS. 7A-7C illustrate yet another example drape 700 and manipulator link 718 in accordance with various embodiments of the present disclosure. As shown, drape 700 is similar to the prior examples, including a sheath 701 and a fluid conduit 716 having a plurality of vents 730 extending within the interior of sheath 701. Drape 700 further includes a guide member 750 coupled to the interior surface of sheath 701. Manipulator link 718 includes an axial cooling channel 734 for routing cooling fluid vented from fluid conduit 716 and an aligning member 752 that is complementary to guide member 750. Guide member 750 and aligning member 752 are engageable with one another. For example, one or both of these engageable components may be provided in the form of complementary magnets (or magnetically attractable material), temporary adhesives, quick couplings, hook-and-loop fasteners, or the like. Further, guide member 750 and aligning member 752 are located on sheath 701 and manipulator link 718 such that their engagement causes vents 730 of fluid conduit 716 to concurrently align with cooling channel 734. Accordingly, these complementary guiding and aligning features facilitate an improved drape installation procedure by reducing the installation time and increasing the accuracy of installation.

Figure 8A:
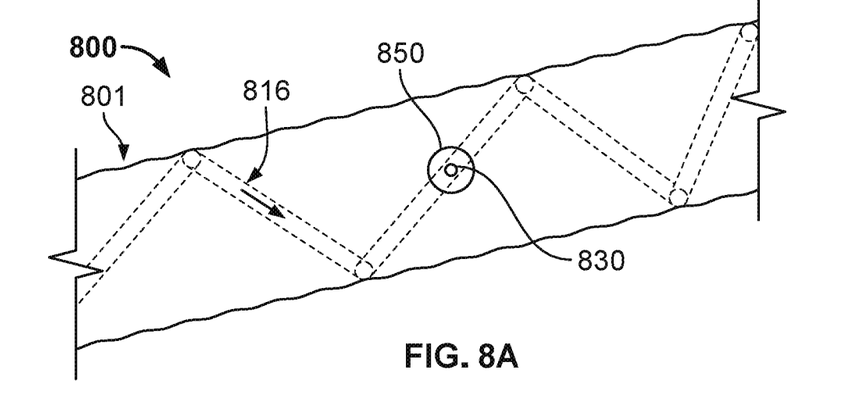
FIG. 8A is a side view of a portion of a seventh example surgical drape having a magnetic member co-located with a helical fluid conduit.
Figure 8B:
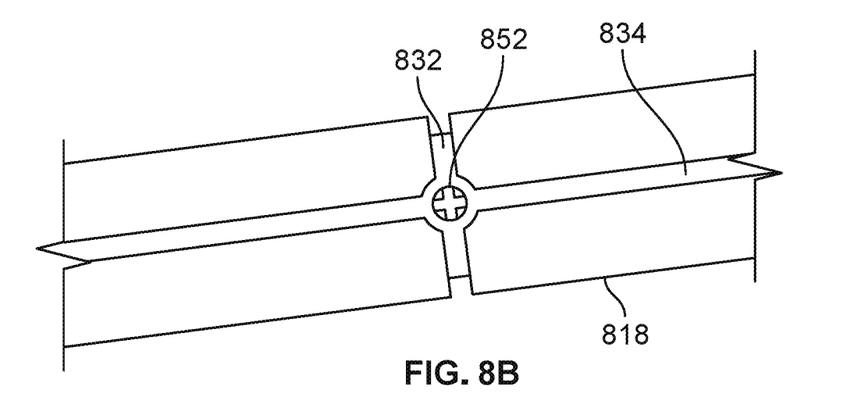
FIG. 8B is a side view of a portion of a fourth surgical instrument manipulator having a magnetic member located at an intersection point of circumferential and axial cooling channels.
Figure 8C:
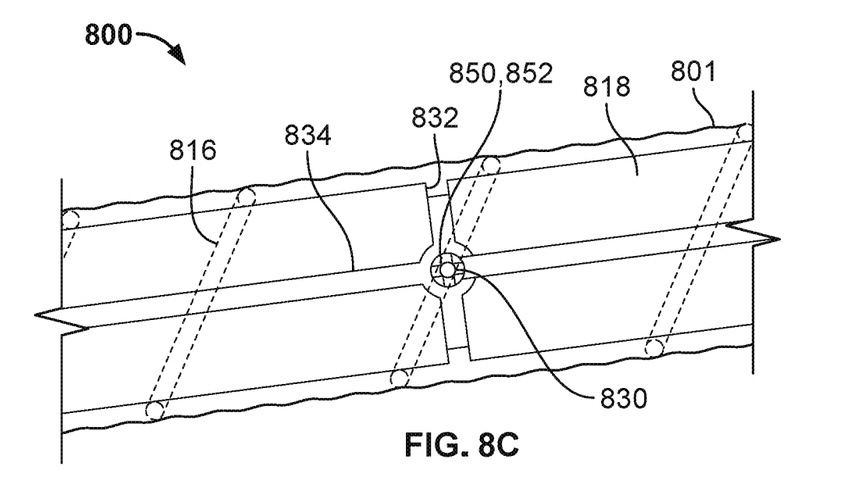
FIG. 8C is a side view of the fourth example manipulator of FIG. 8B carrying the seventh example surgical drape of FIG. 8A.

FIGS. 8A-8C illustrate an example drape 800 and manipulator link 818 similar to the prior example described with reference to FIGS. 7A-7C. Similar to drape 700, drape 800 includes a sheath 801, a fluid conduit 816, and a guide member 850. However, in this example, fluid conduit 816 includes a vent 830 co-located with guide member 850. Accordingly, guide member 850 is designed to permit the flow vented flow of cooling fluid from fluid conduit 816. In this example, guide member 850 includes an orifice that is co-axially located with vent 830. Manipulator link 818 includes circumferential cooling channel 832, axial cooling channel 834, and an aligning member 852 residing at the intersection point between cooling channels 832,834. As described above, guide member 850 and aligning member 852 are appropriately configured to engage one another to facilitate the guided alignment of vent 830 and cooling channels 832,834.

The use of spatially relative terminology throughout the specification and claims is for describing the relative positions and/or orientations of various components of the system and other elements described herein. Unless otherwise stated explicitly, the use of such terminology does not imply a particular position or orientation of the system or any other components relative to the direction of the Earth gravitational force, or the Earth ground surface, or other particular position or orientation that the system other elements may be placed in during operation, manufacturing, and transportation.

A number of embodiments of the invention have been described. Nevertheless, it will be understood that various modifications may be made without departing from the spirit and scope of the inventions. For example, while the embodiments discussed above featured a single fluid conduit, the present disclosure is not so limited. In other embodiments, the surgical drape may include a plurality of conduits, each associated with a respective fluid port and fluid source. In addition, it should be understood that various described components and features optionally may be combined, so that one or more features of one embodiment may be combined with, or substituted for, one or more features of another embodiment consistent with the inventive aspects.

What is claimed is:

1. A surgical system drape comprising:
a sheath having an interior cavity sized to cover a portion of a surgical system manipulator;
an adaptor coupled to the sheath and comprising a manipulator interface and an instrument interface, the manipulator interface configured to couple with a drive interface of the manipulator, and the instrument interface being configured to couple with a drive interface of a surgical instrument mounted to the manipulator; and
a fluid conduit coupled to the sheath and extending within the interior cavity of the sheath, the fluid conduit configured to receive a flow of cooling fluid at a fluid port and convey the fluid along the interior cavity of the sheath to cool a component of a portion of the manipulator, wherein the fluid conduit comprises a passageway having opposing continuous edges defined between two seams attaching adjacent layers of the sheath.

2. The surgical system drape of claim 1, wherein the sheath comprises an impervious structure having interior and exterior surfaces, the interior surface associated with the fluid conduit, and the exterior surface being in a sterile state.

3. The surgical system drape of claim 1, wherein the fluid conduit comprises a tube extending along an interior surface of the sheath.

4. The surgical system drape of claim 1, wherein the sheath comprises an outermost layer, an innermost layer, and a middle layer between the outermost and innermost layers, and wherein the passageway is formed between the middle layer and the innermost layer.

5. The surgical system drape of claim 4, further comprising a hollow sump pocket formed between the outermost layer and the middle layer.

6. The surgical system drape of claim 1, wherein the fluid conduit comprises a vent located adjacent the portion of the manipulator and positioned to expel cooling fluid conveyed by the fluid conduit into contact with the manipulator.

7. The surgical system drape of claim 6, wherein the vent comprises a plurality of apertures distributed along a length of the fluid conduit.

8. The surgical system drape of claim 7, wherein the plurality of apertures is configured to expel more cooling fluid at a first location along the length of the fluid conduit than at a second location, the first location located at a closer proximity to the adaptor than the second location.

9. The surgical system drape of claim 1, wherein at least a portion of the sheath comprises a tubular-shaped structure, and wherein the fluid conduit is arranged in a helical shape traversing the tubular shape along a length of the sheath.

10. The surgical system drape of claim 1, wherein the fluid conduit is configured to provide sufficient structural support to separate the sheath from a surface of the manipulator covered by the sheath.

11. The surgical system drape of claim 10, wherein the fluid conduit is configured to inflate in response to internal pressure of flowing cooling fluid and apply a hoop-stress from the internal pressure to provide the structural support.

12. The surgical system drape of claim 10, wherein the fluid conduit comprises an outer wall having sufficient strength to provide the structural support.

13. The surgical system drape of claim 10, wherein the fluid conduit is arranged to provide less structural support of the sheath adjacent an articulating joint of the manipulator than adjacent a link of the manipulator.

14. The surgical system drape of claim 1, wherein the fluid conduit is shaped to engage a surface feature of the manipulator to align the drape with the manipulator.

15. The surgical system drape of claim 1, further comprising a guide member coupled with the sheath, the guide member configured to engage a portion of the manipulator to self-align one or more vents along the fluid conduit with one or more cooling channels on the manipulator.

16. A surgical system drape comprising:
a sheath having an interior cavity sized to cover a portion of a surgical system manipulator;
an adaptor coupled to the sheath and comprising a manipulator interface and an instrument interface, the manipulator interface configured to couple with a drive interface of the manipulator, and the instrument interface being configured to couple with a drive interface of a surgical instrument mounted to the manipulator; and
a fluid conduit coupled to the sheath and extending within the interior cavity of the sheath, the fluid conduit configured to receive a flow of cooling fluid at a fluid port and convey the fluid along the interior cavity of the sheath to cool a component of a portion of the manipulator, wherein the sheath comprises an outermost layer, an innermost layer, and a middle layer between the outermost layer and the innermost layer, wherein the fluid conduit comprises a passageway formed between the middle layer and the innermost layer.

17. The surgical system drape of claim 16, further comprising a hollow sump pocket formed between the outermost layer and the middle layer.

18. The surgical system drape of claim 16, wherein the sheath comprises:
a plurality of layers comprising the outermost layer and the innermost layer; and
a first seam attaching adjacent layers of the plurality of layers; and
a second seam attaching the adjacent layers of the plurality of layers, wherein the first seam and the second seam define edges of the passageway.

19. The surgical system drape of claim 16, wherein:
the sheath comprises a proximal end portion and a distal end portion and extends from the proximal end portion to the distal end portion; and
the passageway extends helically along the sheath from the proximal end portion of the sheath to the distal end portion of the sheath.

20. The surgical system drape of claim 19, wherein the adaptor is positioned on the distal end portion of the sheath, and the fluid port is positioned on the proximal end portion of the sheath.

21. A surgical system drape comprising:
a sheath having an interior cavity sized to cover a portion of a surgical system manipulator;
an adaptor coupled to the sheath and comprising a manipulator interface and an instrument interface, the manipulator interface configured to couple with a drive interface of the manipulator, the instrument interface being configured to couple with a drive interface of a surgical instrument mounted to the manipulator; and
a fluid conduit coupled to the sheath and extending within the interior cavity of the sheath, the fluid conduit configured to receive a flow of cooling fluid at a fluid port and convey the fluid along the interior cavity of the sheath to cool a component of a portion of the manipulator,
wherein the fluid conduit is arranged in a helical configuration and extends from a proximal end portion of the sheath to a distal end portion of the sheath.

22. The surgical system drape of claim 21, wherein the fluid conduit comprises a tube attached to an interior surface of the sheath.

23. The surgical system drape of claim 21, wherein the fluid conduit comprises a plurality of layers, wherein a first layer of the plurality of layers and a second layer of the plurality of layers define a passageway of the fluid conduit.

24. The surgical system drape of claim 21, wherein the adaptor is positioned on the distal end portion of the sheath, and the fluid port is positioned on the proximal end portion of the sheath.

25. The surgical system drape of claim 21, wherein at least a portion of the sheath comprises a tubular-shaped structure.

26. The surgical system drape of claim 21, wherein the fluid conduit comprises a vent located adjacent the portion of the manipulator and positioned to expel cooling fluid conveyed by the fluid conduit into contact with the manipulator, wherein the vent comprises a plurality of apertures distributed along a length of the fluid conduit.

* * * * *